US00PP16032P3

(12) United States Plant Patent
Hofmann

(10) Patent No.: US PP16,032 P3
(45) Date of Patent: Oct. 11, 2005

(54) **NEW GUINEA *IMPATIENS* PLANT NAMED 'FISUPNIC BURGY'**

(50) Latin Name: *Impatiens hawkeri*
Varietal Denomination: Fisupnic Burgy

(75) Inventor: Birgit C. Hofmann, Bendorf (DE)

(73) Assignee: Florfis AG, Binningen (SE)

( * ) Notice: Subject to any disclaimer, the term of this patent is extended or adjusted under 35 U.S.C. 154(b) by 21 days.

(21) Appl. No.: 10/829,216

(22) Filed: Apr. 22, 2004

(65) Prior Publication Data

US 2004/0216201 P1 Oct. 28, 2004

(30) Foreign Application Priority Data

Apr. 22, 2003 (CH) ..... 03-1994

(51) Int. Cl.[7] ..... A01H 5/00
(52) U.S. Cl. ..... Plt./318
(58) Field of Search ..... Plt./318

(56) References Cited

U.S. PATENT DOCUMENTS

PP11,284 P * 3/2000 Dummen ..... Plt./318
PP13,694 P2 * 4/2003 Hofmann ..... Plt./318
PP14,728 P2 * 4/2004 Hofmann ..... Plt./318
2004/0216201 P1 * 10/2004 Hofmann ..... Plt./318

OTHER PUBLICATIONS

UPOV ROM GTITM Computer Database, GTI Jouve Retrieval Software 2004/06 Citations for 'Fisupnic Burgy'.*

* cited by examiner

*Primary Examiner*—Howard J. Locker
*Assistant Examiner*—W. C. Haas
(74) *Attorney, Agent, or Firm*—Foley & Lardner, LLP

(57) ABSTRACT

A new and distinct cultivar of New Guinea *Impatiens* plant named 'Fisupnic Burgy', and particularly characterized by the combined features of brilliant purple flower color; large, round, butterfly-shaped or slightly cupped flowers; deep green foliage, elliptically shaped leaves; tall, round plant habit, with the flowers borne above the foliage; medium (mid season) beginning of flowering; and well suited both for outdoor planting and for flowering pots.

1 Drawing Sheet

Botanical description: *Impatiens hawkeri.*
Variety denomination: 'Fisupnic Burgy'.

BACKGROUND OF THE INVENTION

The present invention comprises a new and distinct cultivar of *Impatiens* plant, botanically known as *Impatiens hawkeri,* and hereinafter referred to by the cultivar name 'Fisupnic Burgy'.

'Fisupnic Burgy' is a product of a planned breeding program and originated from a hybridization made by the inventor, Birgit C. Hofmann, in a controlled breeding program in Hillscheid, Germany, in the summer of 2000.

The female parent was the variety 'Fisimp 284' (U.S. Plant Pat. No. 13,694), with uniform, purple flowers, deep green foliage, and medium sized, round, dense plant habit.

The male parent was the variety 'Harmony Purple' (unpatented), which is characterized by round, fairly large, red-purple colored flowers, dark green foliage and compact plant habit.

'Fisupnic Burgy' was discovered and selected as one flowering plant within the progeny of the stated cross by the inventor in April 2001 in a green-house in Galdar, Gran Canaria, Spain.

The first act of asexual reproduction of 'Fisupnic Burgy' was accomplished when vegetative cuttings were taken from the initial selection in July 2001 in a controlled environment in Galdar, Spain, by, or under the supervision of the inventor.

Horticultural examination of plants grown from these cuttings initiated in the spring of 2002 in Hillscheid, Germany, and continuing thereafter, has demonstrated that the combination of characteristics as herein disclosed for 'Fisupnic Burgy' are firmly fixed and are retained through successive generations of asexual reproduction. The new cultivar reproduces true to type.

'Fisupnic Burgy' has not been observed under all possible environmental conditions. The phenotype may vary significantly with variations in environment such as temperature, light intensity and day length, without, however, any variation in genotype. The following observations, measurements, and comparisons describe plants grown in Hillscheid, Federal Republic of Germany, under green house conditions which approximate those generally used in commercial practice.

BRIEF SUMMARY OF THE INVENTION

The following traits have been repeatedly observed and are determined to be basic characteristics of 'Fisupnic Burgy', which in combination distinguish this *Impatiens* as a new and distinct cultivar:

1. Brilliant purple flower color;
2. large, round, butterfly-shaped or slightly cupped flowers;
3. deep green foliage, elliptically shaped leaves;
4. tall, round plant habit, with the flowers borne above the foliage;
5. medium (mid season) beginning of flowering; and
6. well suited both for outdoor planting and for flowering pots.

Of the many commercial cultivars known to the inventor, the most similar in comparison to 'Fisupnic Burgy' is the female parental variety 'Fisimp 284' and the male parent 'Harmony Purple'.

In comparison to 'Fisimp 284', 'Fisupnic Burgy' has longer leaves, and larger petals of a slightly less bluish hue. These flowers are borne well above the foliage, while flowers of 'Fisimp 284' are often positioned closer to or between the tips of the leaves. Furthermore, plants of 'Fisupnic Burgy' are considerably taller, by about 30%, than plants of 'Fisimp 284'.

In comparison to 'Harmony Purple', 'Fisupnic Burgy' has taller flowers, larger leaves, less dark green foliage, and a much taller plant habit.

BRIEF DESCRIPTION OF THE PHOTOGRAPHS

The accompanying photographic drawing shows typical flower and foliage characteristics of 'Fisupnic Burgy' with colors being as true as possible with illustrations of this type.

The photographic drawing shows a side view of a typical flowering plant of 'Fisupnic Burgy'.

DETAILED BOTANICAL DESCRIPTION

In the following description color references are made to The Royal Horticultural Society Colour Chart (R.H.S.). The color values were determined indoors from plants growing in a green-house in May 2003, Hillscheid, Germany. The description is based on plants which were planted as rooted cuttings in 12 cm pots in late February 2003 and then grown in the greenhouse at 16° C. minimum temperature. Most observations and measurements were made after the beginning of flowering in mid May, when the plants were about 12 weeks old.

PLANT

General appearance and form:

*Plant habit.*—Tall, uniformly rounded, dense and very well-branched; growth is indeterminate, though weak after beginning of flowering.

*Height.*—20.3 cm.

*Width.*—31.7 cm.

*Number of branches.*—13 to 15.

*Length of branches.*—13 to 16 cm.

*Internode length.*—58 mm.

*Diameter of branches.*—6 to 7 mm.

*Stem color.*—Green, RHS 143 B; brown near the nodes, RHS 184 A.

*Propagation.*—Terminal shoot tips for cuttings.

*Rooting.*—Roots initiate in about 18 days at 22° C., from sticking to transplanting.

*Cultivation time.*—It takes about 9 to 10 weeks to grow a marketable flowering plant in a 12 cm pot.

Foliage:

*Leaf arrangement.*—Primarily in whorls.

*Shape of leaf.*—Elliptic, relatively long, but narrow, with acute base and acuminate tip, surface glossy and slightly rugose.

*Margin.*—Serrulated and ciliated.

*Leaf length.*—16.5 cm.

*Leaf width.*—4.75 cm.

*Upper surface, main color.*—Uniform, deep medium green, no variegation; mature leaves between RHS 137 A and 139 A; young leaves closest to RHS 141 B.

*Vein color.*—Upper surface RHS 181 A; lower surface dull light green, RHS 138 B (both young and mature leaves).

*Veins on lower surface, color.*—From RHS 181 C to 181 D.

*Petiole size.*—20 to 25 mm in length, 3 mm in diameter.

*Petiole, color.*—Upper side brown, from RHS 181A to 184 A; lower side light green, RHS 138 B to 181 C.

INFLORESCENCE

*Flowering response.*—About 9 weeks after planting of rooted cuttings.

*Flowering season.*—Generally indeterminate, mainly from March to October, depending on light intensity.

Flower:

*Number of flowers and buds per node.*—5 to 7, in various stages of development, borne well above the foliage.

*Form of corolla.*—5 petals (single type).

*Shape of corolla.*—Nearly round to faintly zygomorphic, with the petals overlapping, slightly cup-shaped to butterfly-shape; petals are self-cleaning.

*Corolla size.*—Average length 75 mm; average width 72 mm; average depth 10 to 15 mm.

*Petal shape.*—Cordate, top end weakly lobed, with a notch at the top end, base attenuate, margin entire. Petal size: Top petals 32 mm long, 53 mm wide; lateral petals 35 mm long, 30 mm wide; lower petals 38 mm long, 38 mm wide. Texture: Smooth, velvety. Aspect: Flat or slanting upward, top petal may appear curved.

*Color (general tonality from a distance of three meters).*—Uniform, brilliant red purple.

*Color of upper surface.*—RHS 61 B, no markings, the hue may turn somewhat more bluish, to RHS 64 A, with maturing.

*Color of eye zone (base of petals).*—RHS 61 B turning to RHS 64 A with maturing.

*Color of lower surface of petals.*—RHS 67 A.

*Spur.*—One spur per flower, downwardly curved, 55–65 mm long, 2.5 mm in diameter at the flower end; color purple, RHS 53 A.

*Peduncle.*—Flexible, 55 mm in length, 2 mm in diameter; color near flower RHS 181 B, near base green, RHS 145 B.

*Flower bud shape.*—Ovoid, 25 in length, 18 mm in diameter.

*Flower bud color.*—Closest to RHS 61 B.

Reproductive organs:

*Stamens.*—Obovate, 6 mm in diameter, upper surface color is RHS 46 B to 46 C.

*Anthers.*—5 in number, hooded, fused.

*Pollen.*—Pale yellow, about RHS 8 D.

*Style and stigma.*—Five in number, very short, red in color.

*Ovary.*—5-celled, 5 mm long, surface color green, RHS 143 A.

Disease/pest resistance/susceptibility: No observation made to date.

I claim:

1. A new and distinct cultivar of New Guinea *Impatiens* plant named 'Fisupnic Burgy', as described and illustrated herein.

* * * * *

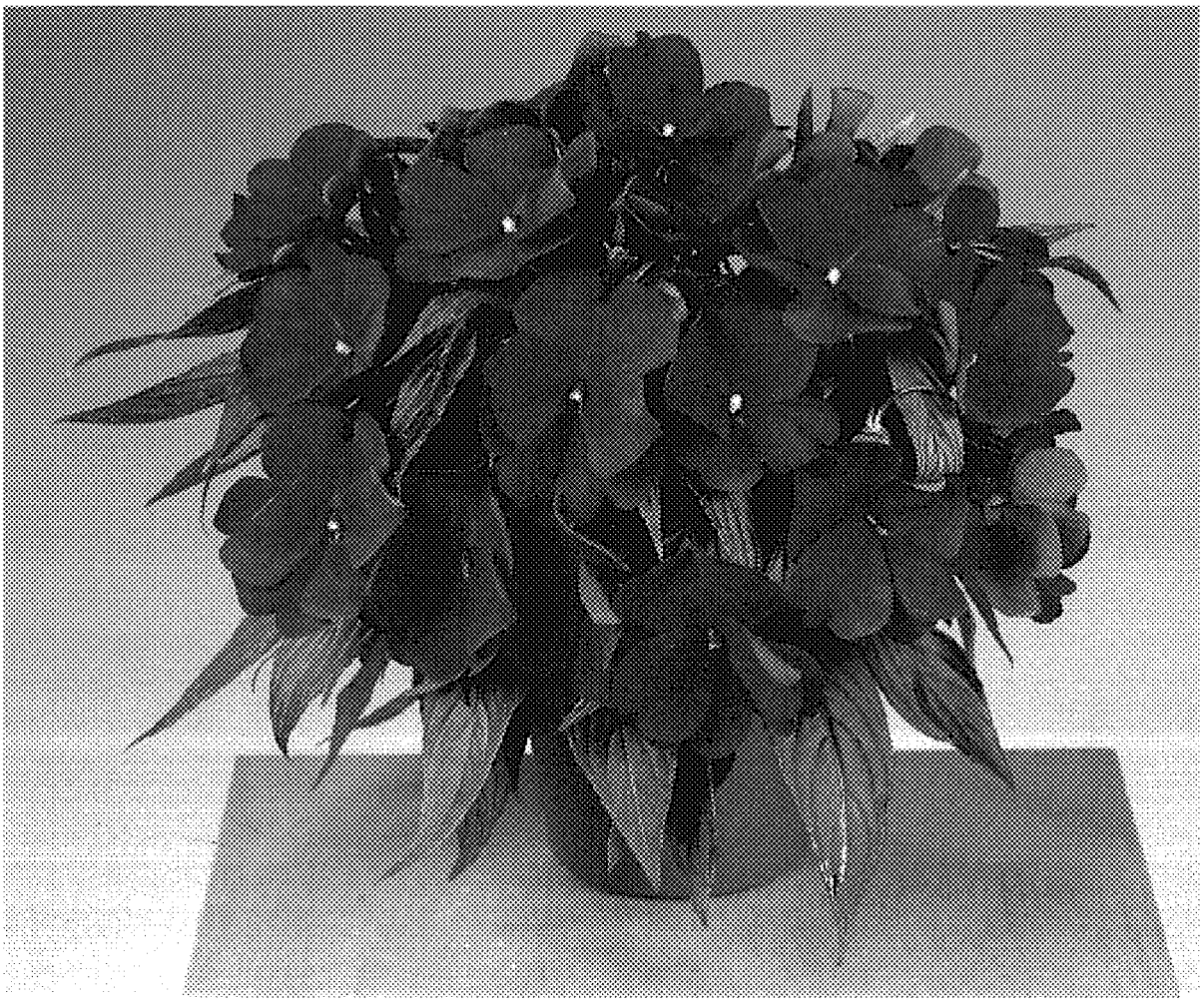

UNITED STATES PATENT AND TRADEMARK OFFICE

CERTIFICATE OF CORRECTION

PATENT NO. : PP 16,032 P3
DATED : October 11, 2005
INVENTOR(S) : Birgit C. Hofmann It is certified that error appears in the above-identified patent and that said Letters Patent is hereby corrected as shown below:

Title page,
Item [73], Assignee, should read -- Florfis AG, Binningen (CH) --.

Signed and Sealed this

Fourth Day of April, 2006

JON W. DUDAS
*Director of the United States Patent and Trademark Office*